United States Patent
Seidling et al.

(10) Patent No.: US 8,846,063 B2
(45) Date of Patent: Sep. 30, 2014

(54) PERSONAL CARE COMPOSITION CONTAINING A VOLATILE AND A TERPENE ALCOHOL

(75) Inventors: Jeffery Richard Seidling, Appleton, WI (US); Sarah Anne Lemke, Appleton, WI (US); Scott W. Wenzel, Neenah, WI (US); Kroy Donald Johnson, Neenah, WI (US); Corey Thomas Cunningham, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 297 days.

(21) Appl. No.: 12/336,297

(22) Filed: Dec. 16, 2008

(65) Prior Publication Data

US 2010/0150971 A1    Jun. 17, 2010

(51) Int. Cl.
| | | |
|---|---|---|
| *A61K 8/02* | (2006.01) | |
| *A61Q 19/00* | (2006.01) | |
| *A61K 8/34* | (2006.01) | |
| *A61K 8/04* | (2006.01) | |
| *A61K 8/70* | (2006.01) | |
| *A61Q 19/10* | (2006.01) | |

(52) U.S. Cl.
CPC . *A61K 8/70* (2013.01); *A61K 8/342* (2013.01); *A61K 8/34* (2013.01); *A61K 8/046* (2013.01); *A61K 8/345* (2013.01); *A61Q 19/10* (2013.01); *A61K 2800/244* (2013.01)
USPC .......................................... 424/401; 510/130

(58) Field of Classification Search
None
See application file for complete search history.

(56) References Cited

U.S. PATENT DOCUMENTS

| | | |
|---|---|---|
| 317,626 A | 5/1885 | Canfield |
| 1,291,073 A | 1/1919 | Miller |
| 2,165,359 A | 7/1939 | Eisenberg |
| 3,574,821 A | 4/1971 | Mediline |
| 3,970,766 A | 7/1976 | Mitchell et al. |
| 3,987,198 A | 10/1976 | Young |
| 3,997,920 A | 12/1976 | Dewoskin |
| 4,078,061 A | 3/1978 | Benson et al. |
| 4,100,324 A | 7/1978 | Anderson et al. |
| 4,221,600 A | 9/1980 | Alexander |
| 4,272,393 A | 6/1981 | Gergely |
| 4,343,783 A | 8/1982 | Hooper et al. |
| 4,388,301 A | 6/1983 | Klein |
| 4,563,473 A | 1/1986 | Hofman et al. |
| 4,617,063 A | 10/1986 | Morris |
| 4,631,752 A | 12/1986 | Heyman et al. |
| 4,790,836 A | 12/1988 | Brecher |
| 4,919,918 A | 4/1990 | Cole et al. |
| 4,942,174 A | 7/1990 | Moeller et al. |
| 5,057,541 A | 10/1991 | Sano et al. |
| 5,152,925 A | 10/1992 | Furman |
| 5,306,439 A | 4/1994 | Lockhart |
| 5,322,683 A | 6/1994 | Mackles et al. |
| 5,429,815 A | 7/1995 | Faryniarz et al. |
| 5,431,841 A | 7/1995 | Lockhart |
| 5,443,817 A | 8/1995 | Zimmerman et al. |
| 5,529,788 A | 6/1996 | De Senna |
| 5,551,989 A | 9/1996 | Mestetsky |
| 5,552,133 A | 9/1996 | Lambert et al. |
| 5,602,091 A | 2/1997 | Monson et al. |
| 5,661,189 A | 8/1997 | Grieveson et al. |
| 5,674,469 A | 10/1997 | Jablonski |
| 5,707,735 A | 1/1998 | Midkiff et al. |
| 5,820,850 A | 10/1998 | Hashimoto et al. |
| 5,824,629 A | 10/1998 | Petritsch |
| 5,855,865 A | 1/1999 | Lambert et al. |
| 5,879,666 A | 3/1999 | Lucas et al. |
| 5,910,493 A | 6/1999 | Golbs et al. |
| 5,911,981 A | 6/1999 | Dahms et al. |
| 5,932,528 A | 8/1999 | Glenn, Jr. et al. |
| 5,965,500 A | 10/1999 | Puvvada |
| 5,993,854 A | 11/1999 | Needleman et al. |
| 6,063,390 A | 5/2000 | Farrell et al. |
| 6,068,857 A | 5/2000 | Weitschies et al. |
| 6,121,215 A | 9/2000 | Rau |

(Continued)

FOREIGN PATENT DOCUMENTS

| | | |
|---|---|---|
| EP | 0 554 213 A1 | 8/1993 |
| EP | 0 927 536 A1 | 7/1999 |

(Continued)

OTHER PUBLICATIONS

Reddy, Kiran et al., "Effervescent Soap Compositions," published at IP.com as Document IPCOM000143580D, Nov. 29, 2006, available online at "http://priorartdatabase.com/IPCOM/000143580", pp. 1-2.

(Continued)

*Primary Examiner* — Brian-Yong Kwon
*Assistant Examiner* — Jennifer A Berrios
(74) *Attorney, Agent, or Firm* — Denise L. Stoker; R. Joseph Foster, III

(57) ABSTRACT

The present disclosure generally relates to a personal care composition containing a carrier, an oil phase having at least one terpene alcohol component, an at least partially fluorinated compound, and a stabilizer. In an exemplary aspect, the at least partially fluorinated compound is stable within the composition of the present disclosure with the introduction of an oil phase having at least one terpene alcohol component to stabilize the at least partially fluorinated compound. Thus, the composition provides an initial foaming action and longer term skin benefits provided by an oil phase contacting a terpene alcohol component. A stabilizing component may also be included to provide further stability to the composition.

23 Claims, No Drawings

(56) References Cited

U.S. PATENT DOCUMENTS

| | | |
|---|---|---|
| 6,136,763 A | 10/2000 | Matsumoto et al. |
| 6,136,768 A | 10/2000 | Dawson et al. |
| 6,177,092 B1 | 1/2001 | Lentini et al. |
| 6,210,062 B1 | 4/2001 | Kokubo |
| 6,217,854 B1 | 4/2001 | Farrell et al. |
| 6,225,299 B1 | 5/2001 | Golbs et al. |
| 6,328,982 B1 * | 12/2001 | Shiroyama et al. ........... 424/401 |
| 6,380,130 B1 | 4/2002 | Meyer et al. |
| 6,391,834 B1 | 5/2002 | Schelges et al. |
| 6,437,040 B2 | 8/2002 | Anthony et al. |
| 6,440,437 B1 | 8/2002 | Krzysik et al. |
| 6,440,912 B2 | 8/2002 | McGee et al. |
| 6,440,923 B1 | 8/2002 | Lyle et al. |
| 6,491,896 B1 | 12/2002 | Rajaiah et al. |
| 6,499,901 B1 | 12/2002 | Rabbani |
| 6,524,594 B1 | 2/2003 | Santora et al. |
| 6,533,873 B1 | 3/2003 | Margosiak et al. |
| 6,541,034 B1 | 4/2003 | Gergely et al. |
| 6,583,103 B1 | 6/2003 | Klinkhammer |
| 6,592,881 B1 | 7/2003 | Fukuda et al. |
| 6,610,312 B2 | 8/2003 | Farrell et al. |
| 6,713,441 B1 | 3/2004 | Desenna et al. |
| 6,716,441 B1 | 4/2004 | Osborne et al. |
| 6,733,765 B2 | 5/2004 | Guillou et al. |
| 6,855,173 B2 | 2/2005 | Ehrnsperger et al. |
| 6,878,380 B2 | 4/2005 | Farrell et al. |
| 2001/0003565 A1 | 6/2001 | McOsker et al. |
| 2001/0010824 A1 | 8/2001 | Handjani et al. |
| 2001/0026792 A1 | 10/2001 | Farrell et al. |
| 2002/0031534 A1 | 3/2002 | Horino |
| 2002/0032133 A1 | 3/2002 | Schelges et al. |
| 2002/0032137 A1 | 3/2002 | Desenna et al. |
| 2002/0039558 A1 | 4/2002 | Farrell et al. |
| 2002/0122772 A1 | 9/2002 | Lukenbach et al. |
| 2002/0128168 A1 | 9/2002 | Lyle et al. |
| 2002/0132746 A1 | 9/2002 | Desenna et al. |
| 2002/0151634 A1 | 10/2002 | Rohrbaugh et al. |
| 2002/0155234 A1 | 10/2002 | Seth |
| 2002/0158361 A1 | 10/2002 | Wulfrath |
| 2002/0192268 A1 | 12/2002 | Alwattari et al. |
| 2002/0197097 A1 | 12/2002 | Rabbani |
| 2003/0007942 A1 | 1/2003 | Koenig |
| 2003/0069165 A1 | 4/2003 | Malton et al. |
| 2003/0083210 A1 | 5/2003 | Goldberg et al. |
| 2003/0099603 A1 | 5/2003 | Rajaiah et al. |
| 2004/0009241 A1 | 1/2004 | Inomata et al. |
| 2004/0018167 A1 | 1/2004 | Lasota |
| 2004/0136864 A1 | 7/2004 | Barham |
| 2004/0136916 A1 * | 7/2004 | Garrison ........................ 424/45 |
| 2004/0147189 A1 | 7/2004 | Smith et al. |
| 2006/0135627 A1 | 6/2006 | Frantz et al. |
| 2007/0141007 A1 | 6/2007 | Glynn et al. |
| 2007/0148101 A1 | 6/2007 | Snyder et al. |
| 2008/0085290 A1 | 4/2008 | Flugge-Berendes et al. |
| 2009/0036856 A1 | 2/2009 | Woltman et al. |

FOREIGN PATENT DOCUMENTS

| | | |
|---|---|---|
| EP | 1 066 827 A2 | 1/2001 |
| JP | 2008-189644 A | 8/2008 |
| WO | WO 93/05819 A1 | 4/1993 |
| WO | WO 96/04018 A1 | 2/1996 |
| WO | WO 96/10988 A1 | 4/1996 |
| WO | WO 96/40279 A2 | 12/1996 |
| WO | WO 03/055456 A1 | 7/2003 |
| WO | WO 2005/103221 A2 | 11/2005 |
| WO | WO 2006/127394 A2 | 11/2006 |
| WO | WO 2007/001341 A2 | 1/2007 |
| WO | WO 2008/039440 A1 | 4/2008 |

OTHER PUBLICATIONS

Limonene, Brief Chemical Encyclopedia, edited by I.L. Knunyants et al., Moscow, vol. 2, 1963, col. 967-968, and English translation.

* cited by examiner

PERSONAL CARE COMPOSITION CONTAINING A VOLATILE AND A TERPENE ALCOHOL

BACKGROUND

1. Field

The present disclosure relates generally to a personal care composition that provides an initial foaming action and additional skin benefits. More particularly, a personal care composition including a volatile compound suspended and incorporated within a personal care composition having at least one terpene alcohol component is disclosed.

2. General Background

Consumer products are often applied to human skin to protect, cleanse and/or treat skin. However, these products can sometimes be harsh on the skin. For example, elderly skin is often dry, itchy, frail and easily torn or bruised. In addition to this, prolonged use of incontinence and occlusive incontinence garments may cause rashes and other skin problems. Rubbing or otherwise manipulating the skin with consumer products can cause tearing and bruising.

A normal routine for a consumer who uses such products is to cleanse, provide an external analgesic (pain relief), and possibly an additional moisturizer. Fragile skin is difficult for an individual or caregiver to touch since it is easily torn and bruised. Also, compromised skin, or skin that is damaged in some way needs to be cleaned and/or moisturized in a sensitive manner. This creates the need to use several different products in multiple deliveries. However, conventional delivery of these consumer products may cause anxiety, additional discomfort or irritation for the individual using the product.

Thus, there is a need to provide cleansing and therapeutic consumer products that can provide numerous benefits to the skin. For example, a product that provides cleansing, cooling effects and pain relief may be useful.

SUMMARY

The present disclosure generally relates to personal care compositions that provide an initial self-foaming action while also providing additional skin benefits, including cleansing and moisturization. A foaming personal care composition containing a carrier, an oil phase containing at least one terpene alcohol component, a volatile such as an at least partially fluorinated compound, and a stabilizer is disclosed. In an exemplary aspect, the at least partially fluorinated compound is stabilized by an oil phase having at least one terpene alcohol component to suspend and incorporate the at least partially fluorinated compound within the foaming personal care composition. The initial foaming action provides a minimal need for rubbing to cleanse and may provide a cooling effect.

In another aspect, the personal care composition is a lotion. The lotion contains a carrier, an oil phase containing at least one terpene alcohol component, a volatile such as an at least partially fluorinated compound, and a stabilizer.

In an exemplary aspect, the terpene alcohol component is selected from linalool, geraniol, citronellol, nerol, α-terpene alcohol, borneol, terpinen-4-ol, limonen-4-ol, carveol, lavandulol, menthol, 8-p-cymenol, pinanol, dihydromyrcenol, myrcenol, dihydrolinalool, isomenthol, neomenthol, isopulegol, trans-p-menthane-3,8-diol, isoborneol, globulol, cedrol, menth-1-en-9-ol, sobrerol, umbellulol, nerolidol, pinanediol, farnesol, frenchyl alcohol, eugenol, phytol, isophytol, phytantriol, and combinations thereof. In a preferred exemplary aspect, the terpene alcohol component may be menthol.

In other exemplary aspects, the terpene alcohol component may be a terpenoid converted to the terpene alcohol component. The terpenoid may be converted to a terpene alcohol by the addition of an acid to the foaming personal care composition.

In other aspects, the personal care composition has between about 0.1% and 20% by weight of the composition of the terpene alcohol component.

In still other aspects, the terpene alcohol component has a ring structure to provide additional stability to the composition.

In an exemplary aspect, the at least partially fluorinated compound is selected from ethyl perfluoroisobutyl ether, ethyl perfluorobutyl ether, methyl perfluoroisobutyl ether, methyl perfluorobutyl ether, perfluorodecalin, perfluorohexylethyl dimethylbutyl ether, perfluorohexane, perfluoroheptane, perfluorodimethylcyclohexane, perfluoromethylcyclohexane, perfluoromethylcyclopentane, perfluorocyclohexyl methanol, and combinations thereof. The foaming personal care composition may contain between about 1% and 40% by weight of the composition of the at least partially fluorinated compound.

In another aspect, the personal care composition has a weight ratio of the at least partially fluorinated compound to the terpene alcohol component between about 2:1 to 40:1.

In exemplary aspects, the stabilizer of the personal care composition may be an emulsifier selected from polysaccharide ethers, polyglycosides, fatty acid derivatives, fatty alcohols, amine oxides, water-soluble cellulose derivatives, alkyl sulfonates, ethoxylated alkyl phenols, alkanolamides, betaines, carboxylated alcohols, carboxylic acids, ethoxylated alcohols, and derivatives and combinations thereof. The emulsifier contains between 0.1% and 20% by weight of the composition.

In other exemplary aspects, the stabilizer of the personal care composition is a structured surfactant system. In an exemplary aspect, the structured surfactant system contains at least one anionic surfactant, and at least one electrolyte. In other embodiments, the structured surfactant system may contain at least one alkanolamide.

In other aspects, the carrier of the personal care composition contains water.

DETAILED DESCRIPTION

The present disclosure generally relates to personal care compositions that provide an initial self-foaming action while also providing additional skin benefits, including cleansing and moisturization. To achieve the initial self-foaming action, a volatile such as an at least partially fluorinated compound is suspended and incorporated within the foaming personal care composition by an oil phase containing at least one terpene alcohol component. Once the at least partially fluorinated compound makes contact with the skin, the composition instantly foams. This at least partially fluorinated compound should not be stable in either a water or oil carrier and the at least partially fluorinated compound should separate out. However, it has been unexpectedly found that the at least partially fluorinated compound is stable within the foaming personal care composition of the present invention by an oil phase containing at least one terpene alcohol component to suspend and incorporate the at least partially fluorinated compound within the foaming personal care composition. An additional stabilizing component may also be included.

In another aspect, the personal care composition is a lotion. The lotion contains a carrier, an oil phase containing at least one terpene alcohol component, a volatile such as an at least partially fluorinated compound, and a stabilizer.

Not to be bound to any particular theory, but it is believed that the at least partially fluorinated compound creates a distinct dispersed phase within the terpene alcohol component of the personal care composition. This is advantageous as the composition allows incorporation of hydrophobic ingredients into a composition. Incorporation of ingredients which are neither soluble in oil or water, such as fluorinated compounds, is then possible.

The personal care composition of the present disclosure allows for a cleansing, external analgesic, moisturizing and cooling composition. The initial foaming action provides a minimal need for rubbing to cleanse and may provide a cooling effect. A built-in moisturizer and analgesic may also be added so that no additional lotion needs to be applied to the skin. The analgesic may provide long-term cooling for the skin. The immediate and long-term cooling effects also create long-term pain relief without further application. Additionally, this approach is advantageous as skin can be moisturized, and normal application of lotion, which can be greasy and can damage skin on application, is not necessary.

In an exemplary aspect, the foaming personal care composition includes an at least partially fluorinated compound. The at least partially fluorinated compounds are volatile compounds having a high vapor pressure that exhibit the best chemical characteristics to facilitate the foaming action of the personal care composition of the present disclosure. The greater the number of carbon-fluorine bonds in the molecule, the greater this desirable behavior. The best compounds for foaming efficiency (i.e. most foaming for least amount of foaming agent needed) contain carbon-carbon, carbon-oxygen, carbon-hydrogen and carbon-fluorine bonds.

The at least partially fluorinated compounds for use in the present disclosure may include ethyl perfluoroisobutyl ether, ethyl perfluorobutyl ether, methyl perfluoroisobutyl ether, methyl perfluorobutyl ether, perfluorodecalin, perfluorohexylethyl dimethylbutyl ether, perfluorohexane, perfluoroheptane, perfluorodimethylcyclohexane, perfluoromethylcyclohexane, perfluoromethylcyclopentane, perfluorocyclohexyl methanol, and combinations thereof. Desirably, the at least partially fluorinated compound includes Cosmetic Fluid CF-76 and Cosmetic Fluid CF-61 (commercially available from 3M Company of St. Paul, Minn.) as the at least partially fluorinated compound.

The personal care composition of the present disclosure may include the at least partially fluorinated compound in an amount of from about 0.5% (by weight of the composition) to about 40% (by weight of the composition), more desirably from about 1% (by weight of the composition) to about 30% (by weight of the composition), and even more desirably from about 10% (by weight of the composition) to about 25% (by weight of the composition).

In an exemplary aspect, the personal care composition includes an oil phase containing at least one terpene alcohol. Terpene alcohols are a well-defined class of compounds that are based on five-carbon isoprene units and have at least one hydroxyl group, which can be primary, secondary, or tertiary. Most terpene alcohols have ten, fifteen, or twenty carbons. The terpene alcohols can be acyclic or cyclic, and saturated or unsaturated, but all are branched. Desirably, the terpene alcohol has a ring structure.

Suitable terpene alcohols include, for example, linalool, geraniol, citronellol, nerol, α-terpene alcohol, borneol, terpinen-4-ol, limonen-4-ol, carveol, lavandulol, menthol, 8-p-cymenol, pinanol, dihydromyrcenol, myrcenol, dihydrolinalool, isomenthol, neomenthol, isopulegol, trans-p-menthane-3,8-diol, isoborneol, globulol, cedrol, menth-1-en-9-ol, sobrerol, umbellulol, nerolidol, pinanediol, farnesol, frenchyl alcohol, eugenol, phytol, isophytol, phytantriol, and combinations thereof. Desirably, menthol is used as the terpene alcohol component.

Terpene alcohols may be found in essential oils. In exemplary aspects, the terpene alcohol component for use with the foaming personal care composition is an essential oil containing a terpene alcohol compound. Exemplary essential oils having a terpene alcohol structure include, but are not limited to, peppermint oil, tea tree oil, cajuput oil, pine oil, and petitgrain oil. Other essential oils having a terpene alcohol structure, as well as other terpene alcohols available as separate entities, are able to stabilize fluorinated component containing systems.

The personal care composition of the present disclosure may include a terpene alcohol component in an amount of from about 0.1% (by weight of the composition) to about 20% (by weight of the composition), more desirably from about 0.5% (by weight of the composition) to about 10% (by weight of the composition), and even more desirably from about 1% (by weight of the composition) to about 10% (by weight of the composition).

In an exemplary aspect, the terpene alcohol component suspends and incorporates the at least partially fluorinated compound in a dose dependent manner. Thus, the amount of terpene alcohol component added to the foaming personal care composition depends on the amount of the at least partially fluorinated compounds. In an exemplary aspect, the foaming personal care composition has a weight ratio of the at least partially fluorinated compound to the terpene alcohol component that is between about 2:1 to 40:1. Desirably, the personal care composition has a weight ratio of the at least partially fluorinated compound to the terpene alcohol component that is about 4:1.

In another exemplary aspect, terpenoids that can be converted to terpene alcohols with the addition of an acid or a base are also able to stabilize volatile, at least partially fluorinated systems. For example, it is believed that a terpenoid, such as 1,8-cineole, may be protonated into alcohol form by addition of an acid or base. Thus, a terpenoid may be used to suspend the at least partially fluorinated compound within the foaming personal care composition.

In an exemplary aspect, the stabilizer for use with the foaming personal care composition contains an emulsifier. In an exemplary aspect, an emulsifier may be selected from anionics, cationics, amphoterics, zwitteronics, and combinations thereof. Exemplary emulsifiers suitable for use with the present disclosure include, but are not limited to, polysaccharide ethers, polyglycosides, fatty acids, fatty alcohols, amine oxides, water-soluble cellulose derivatives, alkyl sulfonates, ethoxylated alkyl phenols, alkanolamides, betaines, zwitterionic surfactants, carboxylated alcohols, carboxylic acids, ethoxylated alcohols, nonionic surfactants such as polysorbate 20 and polysorbate 80, anionic surfactants such as DEA phosphate, cationic surfactants such as behentrimonium methosulfate, and the like and derivatives thereof. It will be appreciated that a single emulsifier or a combination of two or more emulsifiers can be included within the foaming personal care composition of the present invention. The foaming personal care composition of the present disclosure may suitably include one or more emulsifiers in an amount of from about 0.01% (by weight of the composition) to about 20% (by weight of the composition).

Amine oxides are likewise known in the art and are also well suited for use as an emulsifier in the foaming personal care composition of the present invention. Exemplary amine oxides include, but are not limited to, those derivatives formed from the following fatty acids: octyl, decyl, lauryl, cetyl, myristl, stearyl, oleyl, linoleyl and linolenyl. In addition, exemplary amine oxides include, by way of example only, behenamine oxide, cocamine oxide, cocamidopropylamine oxide, and the like.

By way of example only, additional emulsifiers suitable for use in the present invention include sodium deodecylbenzene sulfate, cocamide DEA, cocamidopropyl betaine, oleobetaine, octylphenoxypolyethoxyethanol, and tridecyl ether alcohols.

In another exemplary aspect, the stabilizer for use with the personal care composition contains a structured surfactant system. An exemplary structured surfactant system contains at least one anionic surfactant, and at least one electrolyte. An exemplary structured surfactant system may also include at least one alkanolamide. The composition may further contain water-insoluble particles or partially insoluble components, and/or one or more additional surfactants taken from the categories of anionic surfactants, nonionic surfactants, amphoteric and/or zwitterionic surfactants, and cationic surfactants. The foaming personal care composition of the present disclosure may suitably contain a structured surfactant system in an amount of from about 0.01% (by weight of the composition) to about 50% (by weight of the composition).

The anionic surfactant in the structured surfactant system may be, for example, an aliphatic sulfonate, such as a primary alkane sulfonate, primary alkane disulfonate, alkene sulfonate, hydroxyalkane sulfonate or alkyl glyceryl ether sulfonate, an aromatic sulfonate such as alkyl benzene sulfonate, alkyl sulfate, alkyl ether sulfate, alkyl sulfosuccinates, alkyl and acyl taurates, alkyl and acyl sarcosinates, sulfoacetates, $C_8$-$C_{22}$ alkyl phosphates, alkyl phosphate esters, alkoxyl alkyl phosphate esters, acyl lactates, $C_8$-$C_{22}$ monoalkyl succinates and maleates, and alkyl and acyl isethionates, or a mixture thereof.

The electrolyte can be added separately to the composition or it can be included as part of one of the other raw materials. The electrolyte preferably includes an anion containing phosphate, chloride, sulfate or citrate and a cation containing sodium, ammonium, potassium, magnesium, or mixtures thereof. Some preferred electrolytes are sodium or ammonium chloride and sodium or ammonium sulfate.

The structured surfactant system may also include at least one alkanolamide preferably that has a $C_8$-$C_{24}$ aliphatic chain. The alkanolamide may include one to two alkanol groups which may either have a hydrocarbon backbone or an alkoxy backbone. The hydrocarbon alkanol groups may be $C_2$-$C_4$ straight chain or branched aliphatic groups. The amount of alkanolamide in the composition is about 0.1% to about 10% by weight, and in some aspects is preferably about 2% to about 5% by weight. Some preferred alkanolamides include coco monoethanolamide and coco monoisopropanolamide.

The term alkanolamide is used collectively hereinafter to include long chain aliphatic acid alkanolamides, alkoxy long-chain aliphatic acid alkanolamides, and mixtures thereof. Further, long-chain aliphatic acid alkanolamides may also be referred to in the art as fatty acid alkanolamides.

The personal care composition may also be formulated with one or more conventional pharmaceutically-acceptable and compatible carrier materials. The composition may take a variety of forms including, without limitation, aqueous solutions, gels, balms, lotions, suspensions, creams, milks, salves, ointments, sprays, foams, solid sticks, and the like. Carrier materials suitable for use include those well-known for use in the cosmetic and medical arts as a basis for ointments, lotions, creams, salves, films, aerosols, gels, suspensions, sprays, foams, and the like, and may be used in their art-established levels.

Non-limiting examples of suitable carrier materials include water; glycols such as propylene glycol, butylene glycol, and ethoxydiglycol; lower chain alcohols such as ethanol and isopropanol; glycerin and glycerin derivatives; natural oils such as jojoba oil and sunflower oil; synthetic oils such as mineral oil; silicone derivatives such as cyclomethicone, and other pharmaceutically acceptable carrier materials. As will be recognized by one skilled in the art, the relative amounts of carrier material and other components in the personal care compositions of the disclosure that can be used to formulate the personal care composition will be dictated by the nature of the personal care composition. The levels can be determined by routine experimentation in view of the disclosure provided herein.

In one aspect, the personal care compositions may contain water. The compositions can suitably contain water in an amount of from about 0.1% (by weight of the composition) to about 90% (by weight of the composition), more typically from about 40% (by weight of the composition) to about 90% (by weight of the composition), and more preferably from about 60% (by weight of the composition) to about 90% (by weight of the composition). For instance, where the personal care composition is used in connection with a wet wipe, the personal care composition can suitably contain water in an amount of from about 75% (by weight of the composition) to about 90% (by weight of the composition).

The personal care compositions may further contain additional agents that impart a beneficial effect on skin or hair and/or further act to improve the aesthetic feel of the compositions and wipes described herein. Examples of suitable skin benefit agents include emollients, sterols or sterol derivatives, natural and synthetic fats or oils, viscosity enhancers, rheology modifiers, polyols, surfactants, alcohols, esters, silicones, clays, starch, cellulose, particulates, moisturizers, film formers, slip modifiers, surface modifiers, skin protectants, humectants, sunscreens, and the like.

Thus, in one aspect, the personal care compositions may further optionally include one or more emollients, which typically act to soften, soothe, and otherwise lubricate and/or moisturize the skin. Suitable emollients that can be incorporated into the compositions include oils such as petrolatum based oils, petrolatum, vegetable based oils, mineral oils, natural or synthetic oils, alkyl dimethicones, alkyl methicones, alkyldimethicone copolyols, phenyl silicones, alkyl trimethylsilanes, dimethicone, dimethicone crosspolymers, cyclomethicone, lanolin and its derivatives, fatty esters, glycerol esters and derivatives, propylene glycol esters and derivatives, alkoxylated carboxylic acids, alkoxylated alcohols, fatty alcohols, and combinations thereof.

The personal care compositions of the disclosure can also include additional natural fats and oils. As used herein, the term "natural fat or oil" is intended to include fats, oils, essential oils, essential fatty acids, non-essential fatty acids, phospholipids, and combinations thereof. These natural fats and oils can provide a source of essential and non-essential fatty acids to those found in the skin's natural barrier. Suitable natural fats or oils can include citrus oil, olive oil, avocado oil, apricot oil, babassu oil, borage oil, camellia oil, canola oil, castor oil, coconut oil, corn oil, cottonseed oil, emu oil, evening primrose oil, hydrogenated cottonseed oil, hydrogenated palm kernel oil, jojoba oil, maleated soybean oil, meadowfoam seed oil, palm kernel oil, peanut oil, rapeseed oil, grapeseed oil, safflower oil, sphingolipids, sweet almond oil, tall oil, lauric acid, palmitic acid, stearic acid, linoleic acid, stearyl alcohol, lauryl alcohol, myristyl alcohol, behenyl alcohol, rose hip oil, calendula oil, chamomile oil, eucalyptus oil, juniper oil, sandlewood oil, tea tree oil, sunflower oil, soybean oil, and combinations thereof.

Suitable esters could include, but not be limited to, cetyl palmitate, stearyl palmitate, cetyl stearate, isopropyl laurate, isopropyl myristate, isopropyl palmitate, and combinations thereof. The fatty alcohols could include, but not be limited to, octyldodecanol, lauryl, myristyl, cetyl, stearyl, behenyl alcohol, and combinations thereof. Ethers such as eucalyptol, ceteraryl glucoside, dimethyl isosorbic polyglyceryl-3 cetyl ether, polyglyceryl-3 decyltetradecanol, propylene glycol myristyl ether, and combinations thereof can also suitably be used as emollients.

The personal care composition may include one or more emollient in an amount of from about 0.01% (by weight of the composition) to about 70% (by weight of the composition), more desirably from about 0.05% (by weight of the composition) to about 50% (by weight of the composition), and even more desirably from about 0.10% (by weight of the composition) to about 40% (by weight of the composition). In instances wherein the composition is used in combination with a wet wipe, the composition may include an emollient in an amount of from about 0.01% (by weight of the composition) to about 20% (by weight of the composition), more desirably from about 0.05% (by weight of the composition) to about 10% (by weight of the composition), and more typically from about 0.1% (by weight of the composition) to about 5% (by weight of the composition).

Sterol and sterol derivatives which are suitable for use in the compositions of the present disclosure include, but are not limited to cholesterol, cholesterol sulfate sitosterol, stigmasterol, ergosterol, $C_{10}$-$C_{30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyidecanoate, ergocalciferol, tall oil sterol, soy sterol acetate, lanasterol, soy sterol, polyoxyethelyene soy sterol derivatives, avocado sterols, fatty alcohols, and combinations thereof.

The personal care composition of the invention can also include sterols, sterol derivatives or mixtures of both sterols and sterol derivatives in an amount of from about 0.01% (by weight of the composition) to about 10% (by weight of the composition), more typically from about 0.05% (by weight of the composition) to about 5% (by weight of the composition), and even more typically from about 0.1% (by weight of the composition) to about 1% (by weight of the composition).

Optionally, one or more viscosity enhancers may be added to the personal care composition to increase the viscosity, to help stabilize the composition, such as when the composition is incorporated into a personal care product, thereby reducing migration of the composition and improving transfer to the skin. Suitable viscosity enhancers include polyolefin resins, lipophilic/oil thickeners, ethylene/vinyl acetate copolymers, polyethylene, silica, silica silylate, silica methyl silylate, colloidal silicone dioxide, cetyl hydroxy ethyl cellulose, other organically modified celluloses, PVP/decane copolymer, PVM/MA decadiene crosspolymer, PVP/eicosene copolymer, PVP/hexadecane copolymer, clays, carbomers, acrylic based thickeners, surfactant thickeners, and combinations thereof.

The personal care composition may desirably include one or more viscosity enhancers in an amount of from about 0.01% (by weight of the composition) to about 25% (by weight of the composition), more desirably from about 0.05% (by weight of the composition) to about 10% (by weight of the composition), and even more desirably from about 0.1% (by weight of the composition) to about 5% (by weight of the composition).

The personal care compositions of the disclosure may optionally further contain rheology modifiers. Rheology modifiers may help increase the melt point viscosity of the composition so that the composition readily remains on the surface of a personal care product.

Suitable rheology modifiers include combinations of α-olefins and styrene alone or in combination with mineral oil or petrolatum, combinations of di-functional α-olefins and styrene alone or in combination with mineral oil or petrolatum, combinations of α-olefins and isobutene alone or in combination with mineral oil or petrolatum, ethylene/propylene/styrene copolymers alone or in combination with mineral oil or petrolatum, butylene/ethylene/styrene copolymers alone or in combination with mineral oil or petrolatum, ethylene/vinyl acetate copolymers, polyethylene polyisobutylenes, polyisobutenes, polyisobutylene, dextrin palmitate, dextrin palmitate ethylhexanoate, stearoyl inulin, stearalkonium bentonite, distearadimonium hectorite, stearalkonium hectorite, styrene/butadiene/styrene copolymers, styrene/isoprene/styrene copolymers, styrene-ethylene/butylene-styrene copolymers, styrene-ethylene/propylene-styrene copolymers, (styrene-butadiene)n polymers, (styrene-isoprene)n polymers, styrene-butadiene copolymers, styrene-ethylene/propylene copolymers and combinations thereof. Specifically, rheology enhancers such as mineral oil and ethylene/propylene/styrene copolymers, and mineral oil and butylene/ethylene/styrene copolymers (Versagel blends from Penreco) are particularly preferred. Also, Vistanex (Exxon) and Presperse (Amoco) polymers are particularly suitable rheology modifiers.

The personal care composition of the disclosure can suitably include one or more rheology modifier in an amount of from about 0.1% (by weight of the composition) to about 5% (by weight of the composition).

The personal care compositions of the disclosure may optionally further contain humectants. Examples of suitable humectants include glycerin, glycerin derivatives, sodium hyaluronate, betaine, amino acids, glycosaminoglycans, honey, sorbitol, glycols, polyols, sugars, hydrogenated starch hydrolysates, salts of PCA, lactic acid, lactates, and urea. A particularly preferred humectant is glycerin. The composition of the present disclosure may suitably include one or more humectant in an amount of from about 0.05% (by weight of the composition) to about 25% (by weight of the composition).

The personal care compositions of the disclosure may optionally further contain moisturizers. Examples of suitable moisturizers include light hydrocarbon oil (e.g., mineral oil, isododecane, petrolatum), vegetable or natural oil (e.g., sunflower oil, olive oil, sweet almond oil, grapeseed oil, corn oil, safflower oil, shea butter, coconut oil, canola oil, castor oil, jojoba oil), hydrogenated vegetable oil (e.g., hydrogenated castor wax, hydrogenated apricot kernel oil, hydrogenated canola oil, hydrogenated jojoba oil, hydrogenated olive oil, hydrogenated sesame seed oil), fatty ester (e.g., octyldodecyl neopentanoate, stearyl stearate, isopropyl myristate, isopropyl palmitate, stearyl behenate, $C_{12}$-$C_{15}$ alkyl benzoate, butyl isostearate, cetyl caprate, cetyl caprylate, ethyl apricot kernelate, ethyl avocadate, ethylhexyl caprate/caprylate, ethylhexyl cocoate, ethylhexyl isopalmitate, isocetyl myristate, isopropyl jojobate, myristyl laurate), fatty acid (e.g., palmitic acid, stearic acid, myristic acid, oleic acid, linoleic acid, behenic acid), fatty alcohol (e.g., lauryl alcohol, cetyl alcohol, stearyl alcohol, behenyl alcohol), or combinations thereof. In one aspect, the composition may contain a fatty ester as a carrier. One example of a fatty ester is isopropyl myristate, which is available under the name TEGOSOFT M (Evonik). The composition of the present disclosure may suitably include one or more moisturizer in an amount of from about 0.01% (by weight of the composition) to about 50% (by weight of the composition).

The personal care compositions of the disclosure may optionally further contain film formers. Examples of suitable film formers include lanolin derivatives (e.g., acetylated lanolins), superfatted oils, cyclomethicone, cyclopentasiloxane, dimethicone, natural and synthetic oils, fatty acids, fatty alcohols, waxes, synthetic and biological polymers, proteins, quaternary ammonium materials, starches, gums, cellulosics, polysaccharides, albumen, acrylates derivatives, IPDI derivatives, and the like. The composition of the present disclosure may suitably include one or more film former in an amount of from about 0.01% (by weight of the composition) to about 20% (by weight of the composition).

The personal care compositions of the disclosure may optionally further contain surface modifiers. Examples of suitable surface modifiers include silicones, quaternium materials, powders, salts, peptides, polymers, clays, and glyceryl esters. The composition of the present disclosure may suitably include one or more surface modifier in an amount of from about 0.01% (by weight of the composition) to about 20% (by weight of the composition).

The personal care compositions of the disclosure may optionally further contain skin protectants. Examples of suitable skin protectants include ingredients referenced in SP monograph (21 CFR §347). Suitable skin protectants and amounts include those set forth in SP monograph, Subpart B—Active Ingredients §347.10: (a) Allantoin, 0.5 to 2%, (b) Aluminum hydroxide gel, 0.15 to 5%, (c) Calamine, 1 to 25%, (d) Cocoa butter, 50 to 100%, (e) Cod liver oil, 5 to 13.56%, in accordance with §347.20(a)(1) or (a)(2), provided the product is labeled so that the quantity used in a 24-hour period does not exceed 10,000 U.S.P. Units vitamin A and 400 U.S.P. Units cholecalciferol, (f) Colloidal oatmeal, 0.007% minimum; 0.003% minimum in combination with mineral oil in accordance with §347.20(a)(4), (g) Dimethicone, 1 to 30%, (h) Glycerin, 20 to 45%, (i) Hard fat, 50 to 100%, (j) Kaolin, 4 to 20%, (k) Lanolin, 12.5 to 50%, (l) Mineral oil, 50 to 100%; 30 to 35% in combination with colloidal oatmeal in accordance with §347.20(a)(4), (m) Petrolatum, 30 to 100%, (o) Sodium bicarbonate, (q) Topical starch, 10 to 98%, (r) White petrolatum, 30 to 100%, (s) Zinc acetate, 0.1 to 2%, (t) Zinc carbonate, 0.2 to 2%, (u) Zinc oxide, 1 to 25%.

The personal care compositions of the disclosure may optionally further contain particulates. Examples of suitable particulates include bismuth oxychloride, iron oxide, mica, surface treated mica, ZnO, $ZrO_2$, silica, silica silyate, colloidal silica, attapulgite, sepiolite, starches (i.e., corn, tapioca, rice), cellulosics, nylon-12, nylon-6, polyethylene, talc, styrene, polystyrene, polypropylene, ethylene/acrylic acid copolymer, acrylates, acrylate copolymers (methylmethacrylate crosspolymer), sericite, titanium dioxide, aluminum oxide, silicone resin, barium sulfate, clays, cellulosics, calcium carbonate, cellulose acetate, polymethyl methacrylate, polymethylsilsequioxane, talc, tetrafluoroethylene, silk powder, boron nitride, lauroyl lysine, aluminum starch octenylsuccinate, and calcium starch octenylsuccinate. The personal care composition of the present disclosure may suitably include one or more particulate in an amount of from about 0.01% (by weight of the composition) to about 20% (by weight of the composition).

The personal care compositions of the disclosure may optionally further contain sunscreens. Examples of suitable sunscreens include aminobenzoic acid, avobenzone, cinoxate, dioxybenzone, homosalate, menthyl anthranilate, octocrylene, octinoxate, octisalate, oxybenzone, padimate O, phenylbenzimidazole sulfonic acid, sulisobenzone, titanium dioxide, trolamine salicylate, zinc oxide, and combinations thereof. Other suitable sunscreens and amounts include those approved by the FDA, as described in the Final Over-the-Counter Drug Products Monograph on Sunscreens (Federal Register, 1999:64:27666-27693), herein incorporated by reference, as well as European Union approved sunscreens and amounts.

The personal care compositions of the disclosure may optionally further contain quaternary ammonium materials. Examples of suitable quaternary ammonium materials include polyquaternium-7, polyquaternium-10, benzalkonium chloride, behentrimonium methosulfate, cetrimonium chloride, cocamidopropyl pg-dimonium chloride, guar hydroxypropyltrimonium chloride, isostearamidopropyl morpholine lactate, polyquaternium-33, polyquaternium-60, polyquaternium-79, quaternium-18 hectorite, quaternium-79 hydrolyzed silk, quaternium-79 hydrolyzed soy protein, rapeseed amidopropyl ethyldimonium ethosulfate, silicone quaternium-7, stearalkonium chloride, palmitamidopropyltrimonium chloride, butylglucosides, hydroxypropyltrimonium chloride, laurdimoniumhydroxypropyl decylglucosides chloride, and the like. The personal care composition of the present disclosure may suitably include one or more quaternary material in an amount of from about 0.01% (by weight of the composition) to about 20% (by weight of the composition).

The personal care composition of the present disclosure may include one or more surfactants. Examples of suitable surfactants include, for example, anionic surfactants, cationic surfactants, amphoteric surfactants, zwitterionic surfactants, non-ionic surfactants, and combinations thereof. Specific examples of suitable surfactants are known in the art and include those suitable for incorporation into personal care compositions and wipes. The composition of the present disclosure may suitably include one or more surfactant in an amount of from about 0.01% (by weight of the composition) to about 20% (by weight of the composition).

The personal care compositions of the present disclosure may additionally include adjunct components conventionally found in pharmaceutical compositions in their art-established fashion and at their art-established levels. For example, the compositions may contain additional compatible pharmaceutically active materials for combination therapy, such as antimicrobials, antioxidants, anti-parasitic agents, antipruritics, antifungals, antiseptic actives, biological actives, astringents, keratolytic actives, local anaesthetics, anti-stinging agents, anti-reddening agents, skin soothing agents, and combinations thereof. Other suitable additives that may be included in the compositions of the present disclosure include colorants, deodorants, fragrances, perfumes, emulsifiers, lubricants, natural moisturizing agents, skin conditioning agents, skin protectants and other skin benefit agents (e.g., extracts such as aloe vera and anti-aging actives such as peptides), solvents, solubilizing agents, suspending agents, wetting agents, humectants, preservatives, propellants, pH adjusters, buffering agents and buffering systems, dyes and/or pigments, and combinations thereof.

As various changes could be made in the above personal care compositions and substrates/articles without departing from the scope of the disclosure, it is intended that all matter contained in the above description shall be interpreted as illustrative and not in a limiting sense.

EXAMPLES

The following non-limiting examples are provided to further illustrate the present disclosure.

Example 1

In this example, a personal care composition formulated with an oil phase containing a terpene alcohol and an at least partially fluorinated compound was prepared. The composition components are listed in Table 1.

TABLE 1

Example Composition A

| Trade name | INCI name | Composition Wt. % |
|---|---|---|
| Water | Water | 30.5% |
| Structure XL | Hydroxypropyl Starch Phosphate | 3.0% |
| Xanthan Gum | Xanthan Gum | 0.35% |
| Ultragel 300 | Polyquaternium-37 | 0.1% |
| Glycerin | Glycerin | 1.0% |
| Miracare SLB 205 | Water, Sodium Trideceth Sulfate, Sodium Lauroamphoacetate, Sodium Chloride, Methylisothiazolinone | 35% |
| 3M Cosmetic Fluid CF-76 | Ethyl Perfluorobutyl Ether, Ethyl Perfluoroisobutyl Ether | 19.5% |
| Florasun 90 | *Helianthus Annus* (Sunflower) Oil | 2.5% |
| Menthol | Menthol | 5.0% |
| Butylated Hydroxytoluene | BHT | 0.05% |
| Sodium Benzoate | Sodium Benzoate | 0.5% |
| Sodium Chloride | Sodium Chloride | 2.5% |
| Citric Acid | Citric Acid | q.s. pH 4.7 |

To prepare Example Composition A, water is added to a vessel. The polyquaternium-37 was then added and mixed with the water until uniform. Hydroxypropyl starch phosphate was then added and mixed until uniform. The xanthan gum was then added, and the resulting mixture was mixed until uniform. The structured surfactant blend, Miracare SLB 205, was then added and the resulting mixture was mixed until uniform to prepare a surfactant phase. In a separate vessel, the menthol, the terpene alcohol component, and sunflower oil was added to butylated hydroxytoluene and mixed until the butylated hydroxytoluene melted (heat to 50° C. if necessary) to prepare an oil phase. The oil phase were then added to the surfactant phase. Subsequently, the Cosmetic Fluid, salt and sodium benzoate were added, and the resulting mixture was mixed until uniform. The pH of Composition A was adjusted to about 4.7 using citric acid.

Example Composition A described in Table 1 did not spontaneously form bubbles while processing and maintained its cohesiveness upon dispensing onto an inanimate surface such as a table top or into a plastic weigh boat. Upon dispensing and rubbing onto the hand, the Composition A spontaneously formed foam created by the volatile Cosmetic Fluid boiling at skin temperature and bubbling through the surfactant blend.

Example 2

Comparative

In this example, a composition containing an at least partially fluorinated compound without an oil phase containing at least one terpene alcohol was prepared. The composition components are listed in Table 2.

TABLE 2

Comparative Composition B

| Trade name | INCI name | Composition Wt. % |
|---|---|---|
| Water | Water | 30.55% |
| Structure XL | Hydroxypropyl Starch Phosphate | 3.0% |
| Xanthan Gum | Xanthan Gum | 0.35% |
| Ultragel 300 | Polyquaternium-37 | 0.1% |
| Glycerin | Glycerin | 1.0% |
| Miracare SLB 205 | Water, Sodium Trideceth Sulfate, Sodium Lauroamphoacetate, Sodium Chloride, Methylisothiazolinone | 35% |
| 3M Cosmetic Fluid CF-76 | Ethyl Perfluorobutyl Ether, Ethyl Perfluoroisobutyl Ether | 27% |
| Sodium Benzoate | Sodium Benzoate | 0.5% |
| Sodium Chloride | Sodium Chloride | 2.5% |
| Citric Acid | Citric Acid | q.s. pH 4.7 |

To prepare Comparative Composition B, water is added to a vessel. The polyquaternium-37 was then added and mixed with the water until uniform. Hydroxypropyl starch phosphate was then added and mixed until uniform. The xanthan gum was then added, and the resulting mixture was mixed until uniform. The structured surfactant blend, Miracare SLB 205, was then added and the resulting mixture was mixed until uniform to prepare a surfactant phase. Subsequently, the Cosmetic Fluid, salt and sodium benzoate were added to the surfactant phase, and the resulting mixture was mixed until uniform. The pH of Comparative Composition B was adjusted to about 4.7 using citric acid, as needed.

Comparative Composition B spontaneously foamed during the mixing procedure. Upon completion of the composition procedure, the composition did not maintain cohesiveness and spontaneously foamed continually. Thus, it is shown that an oil phase with at least one terpene alcohol component is necessary to suspend and incorporate the at least partially fluorinated compounds within the composition.

Example 3

Comparative

In this example, a composition was prepared containing an at least partially fluorinated compound without the oil phase containing at least one terpene alcohol. A smaller amount of the at least partially fluorinated compound phase was included. The composition components are listed in Table 3.

TABLE 3

Comparative Composition C

| Trade name | INCI name | Composition Wt. % |
|---|---|---|
| Water | Water | 49.65% |
| Structure XL | Hydroxypropyl Starch Phosphate | 3.0% |
| Xanthan Gum | Xanthan Gum | 0.35% |
| Ultragel 300 | Polyquaternium-37 | 0.1% |
| Glycerin | Glycerin | 1.0% |
| Miracare SLB 205 | Water, Sodium Trideceth Sulfate, Sodium Lauroamphoacetate, Sodium | 35% |

TABLE 3-continued

Comparative Composition C

| Trade name | INCI name | Composition Wt. % |
|---|---|---|
|  | Chloride, Methylisothiazolinone |  |
| 3M Cosmetic Fluid CF-76 | Ethyl Perfluorobutyl Ether, Ethyl Perfluoroisobutyl Ether | 7% |
| Sodium Benzoate | Sodium Benzoate | 0.5% |
| Sodium Chloride | Sodium Chloride | 2.5% |
| Citric Acid | Citric Acid | q.s. pH 4.7 |

To prepare Comparative Composition C, water is added to a vessel. The polyquaternium-37 was then added and mixed with the water until uniform. Hydroxypropyl starch phosphate was then added and mixed until uniform. The xanthan gum was then added, and the resulting mixture was mixed until uniform. The structured surfactant blend, Miracare SLB 205, was then added and the resulting mixture was mixed until uniform to prepare a surfactant phase. Subsequently, the Cosmetic Fluid, salt and sodium benzoate were added to the surfactant phase, and the resulting mixture was mixed until uniform. The pH of Comparative Composition C was adjusted to about 4.7 using citric acid, as needed.

Comparative Composition C spontaneously foamed during and after the mixing process. The composition did foam at a slower rate, but was not stabilized, illustrating that even with lower amounts of the at least partially fluorinated compound, an oil phase with a terpene alcohol component is needed to stabilize the composition.

Example 4

In this example, a composition was prepared containing an at least partially fluorinated compound and an oil phase. However, the oil phase did not have a component having at least one terpene alcohol. The composition components are listed in Table 4.

TABLE 4

Comparative Composition D

| Trade name | INCI name | Composition Wt. % |
|---|---|---|
| Water | Water | 30.5% |
| Structure XL | Hydroxypropyl Starch Phosphate | 3.0% |
| Xanthan Gum | Xanthan Gum | 0.35% |
| Ultragel 300 | Polyquaternium-37 | 0.1% |
| Glycerin | Glycerin | 1.0% |
| Miracare SLB 205 | Water, Sodium Trideceth Sulfate, Sodium Lauroamphoacetate, Sodium Chloride, Methylisothiazolinone | 35% |
| 3M Cosmetic Fluid CF-76 | Ethyl Perfluorobutyl Ether, Ethyl Perfluoroisobutyl Ether | 19.5% |
| Florasun 90 | *Helianthus Annus* (Sunflower) Oil | 7.5% |
| Butylated Hydroxytoluene | BHT | 0.05% |
| Sodium Benzoate | Sodium Benzoate | 0.5% |
| Sodium Chloride | Sodium Chloride | 2.5% |
| Citric Acid | Citric Acid | q.s. pH 4.7 |

To prepare Comparative Composition D, water is added to a vessel. The polyquaternium-37 was then added and mixed with the water until uniform. Hydroxypropyl starch phosphate was then added and mixed until uniform. The xanthan gum was then added, and the resulting mixture was mixed until uniform. The structured surfactant blend, Miracare SLB 205, was then added and the resulting mixture was mixed until uniform to prepare a surfactant phase. In a separate vessel, sunflower oil was added to butylated hydroxytoluene and mixed until the butylated hydroxytoluene melted (heat to 50° C. if necessary) to prepare an oil phase. The oil phase was then added to the surfactant phase. Subsequently, the Cosmetic Fluid, salt and sodium benzoate were added to the surfactant phase, and the resulting mixture was mixed until uniform. The pH of Comparative Composition D was adjusted to about 4.7 using citric acid, as needed.

Comparative Composition D is not stable during or after the mixing process. If placed into an airtight container, it retains its lotion texture, but as soon as the headspace is opened to the atmosphere, the composition starts to spontaneously bubble. Thus, Example Composition 4 illustrates that the oil phase must contain at least one terpene alcohol structure to stabilize the at least partially fluorinated compound.

Examples 5-7

In this example, personal care compositions containing an oil phase having a terpene alcohol at different concentrations and an at least partially fluorinated compound were prepared. The composition components are listed in Table 5.

TABLE 5

Example Composition E-G

| Trade name | INCI name | Composition Wt. % |
|---|---|---|
| Water | Water | q.a. to 100% |
| Structure XL | Hydroxypropyl Starch Phosphate | 3.0% |
| Xanthan Gum | Xanthan Gum | 0.35% |
| Ultragel 300 | Polyquaternium-37 | 0.1% |
| Glycerin | Glycerin | 1.0% |
| Miracare SLB 205 | Water, Sodium Trideceth Sulfate, Sodium Lauroamphoacetate, Sodium Chloride, Methylisothiazolinone | 35% |
| 3M Cosmetic Fluid CF-76 | Ethyl Perfluorobutyl Ether, Ethyl Perfluoroisobutyl Ether | 19.5% |
| Florasun 90 | *Helianthus Annus* (Sunflower) Oil | 2.5% |
| Menthol | Menthol | X % |
| Butylated Hydroxytoluene | BHT | 0.05% |
| Sodium Benzoate | Sodium Benzoate | 0.5% |
| Sodium Chloride | Sodium Chloride | 2.5% |
| Citric Acid | Citric Acid | q.s. pH 4.7 |

To prepare Example Compositions E, F, G, water is added to a vessel. The polyquaternium-37 was then added and mixed with the water until uniform. Hydroxypropyl starch phosphate was then added and mixed until uniform. The xanthan gum was then added, and the resulting mixture was mixed until uniform. The structured surfactant blend, Miracare SLB 205, was then added and the resulting mixture was mixed until uniform to prepare a surfactant phase. In a separate vessel, menthol, the terpene alcohol component, was added at weight concentrations of 0.5%, 1.0%, and 2.5% to Example Compositions E, F, and G respectively, to sunflower oil and added to butylated hydroxytoluene and mixed until the butylated hydroxytoluene melted (heat to 50° C. if necessary) to prepare an oil phase. The oil phase was then added to the surfactant phase. Subsequently, the Cosmetic Fluid, salt and sodium benzoate were added, and the resulting mixture was mixed until uniform. The pH of Example Compositions E, F, and G were adjusted to about 4.7 using citric acid, as needed.

It was discovered that none of the three prepared Example Compositions E, F, and G having lower concentrations of menthol performed as well as Example Composition A containing 5% menthol at stabilizing the at least partially fluorinated compound. Thus, there is a dose dependent response to the terpene alcohol in the compositions made with smaller amounts of a terpene alcohol illustrating some lost cohesiveness and initial spontaneous foaming more quickly than those with higher amounts of a terpene alcohol. While the lower concentration of terpene alcohols still stabilized the at least partially fluorinated compounds, a weight ratio based on the weight of the composition of about 4:1 of fluorinated compounds to terpene alcohols best stabilized the system.

Example 8

In this example, personal care compositions containing an oil phase having an alternative terpene alcohol and an at least partially fluorinated compound were prepared. The composition components are listed in Table 6.

TABLE 6

Example Composition H

| Trade name | INCI name | Composition Wt. % |
|---|---|---|
| Water | Water | 28% |
| Structure XL | Hydroxypropyl Starch Phosphate | 3.0% |
| Xanthan Gum | Xanthan Gum | 0.35% |
| Ultragel 300 | Polyquaternium-37 | 0.1% |
| Glycerin | Glycerin | 1.0% |
| Miracare SLB 205 | Water, Sodium Trideceth Sulfate, Sodium Lauroamphoacetate, Sodium Chloride, Methylisothiazolinone | 35% |
| 3M Cosmetic Fluid CF-76 | Ethyl Perfluorobutyl Ether, Ethyl Perfluoroisobutyl Ether | 19.5% |
| Peppermint Oil | Peppermint Oil | 10.0% |
| Butylated Hydroxytoluene | BHT | 0.05% |
| Sodium Benzoate | Sodium Benzoate | 0.5% |
| Sodium Chloride | Sodium Chloride | 2.5% |
| Citric Acid | Citric Acid | q.s. pH 4.7 |

To prepare Example Composition H, water is added to a vessel. The polyquaternium-37 was then added and mixed with the water until uniform. Hydroxypropyl starch phosphate was then added and mixed until uniform. The xanthan gum was then added, and the resulting mixture was mixed until uniform. The structured surfactant blend, Miracare SLB 205, was then added and the resulting mixture was mixed until uniform to prepare a surfactant phase. In a separate vessel, peppermint oil, including 45% by weight menthol, the terpene alcohol component, was added to butylated hydroxytoluene and mixed until the butylated hydroxytoluene melted (heat to 50° C. if necessary) to prepare an oil phase. The oil phase was then added to the surfactant phase. Subsequently, the Cosmetic Fluid, salt and sodium benzoate were added, and the resulting mixture was mixed until uniform. The pH of Example Composition H was adjusted to about 4.7 using citric acid, as needed.

Example Composition H described in Table 6 went together very well with no instability detected during the mixing process. The same stability profile as Example Composition H is achieved with no spontaneous foam detected when the product is in the beaker, nor when it is expressed onto a surface. Bubbling does occur when the product is placed onto warm hands and rubbed gently.

Example 9

In this example, personal care compositions containing an oil phase having a terpene with a similar shape to menthol and an at least partially fluorinated compound were prepared. The composition components are listed in Table 7.

TABLE 7

Example Composition I

| Trade name | INCI name | Composition Wt. % |
|---|---|---|
| Water | Water | 28% |
| Structure XL | Hydroxypropyl Starch Phosphate | 3.0% |
| Xanthan Gum | Xanthan Gum | 0.35% |
| Ultragel 300 | Polyquaternium-37 | 0.1% |
| Glycerin | Glycerin | 1.0% |
| Miracare SLB 205 | Water, Sodium Trideceth Sulfate, Sodium Lauroamphoacetate, Sodium Chloride, Methylisothiazolinone | 35% |
| 3M Cosmetic Fluid CF-76 | Ethyl Perfluorobutyl Ether, Ethyl Perfluoroisobutyl Ether | 19.5% |
| D-Limonene | D-Limonene | 10.0% |
| Butylated Hydroxytoluene | BHT | 0.05% |
| Sodium Benzoate | Sodium Benzoate | 0.5% |
| Sodium Chloride | Sodium Chloride | 2.5% |
| Citric Acid | Citric Acid | q.s. pH 4.7 |

To prepare Example Composition I, water is added to a vessel. The polyquaternium-37 was then added and mixed with the water until uniform. Hydroxypropyl starch phosphate was then added and mixed until uniform. The xanthan gum was then added, and the resulting mixture was mixed until uniform. The structured surfactant blend, Miracare SLB 205, was then added and the resulting mixture was mixed until uniform to prepare a surfactant phase. In a separate vessel, limonene was added to butylated hydroxytoluene and mixed until the butylated hydroxytoluene melted (heat to 50° C. if necessary) to prepare an oil phase. The oil phase was then added to the surfactant phase. Subsequently, the Cosmetic Fluid, salt and sodium benzoate were added, and the resulting mixture was mixed until uniform. The pH of Example Composition I was adjusted to about 4.7 using citric acid, as needed.

Example Composition I described in Table 7 displayed instability both in processing and following the mixing process. Spontaneous foaming was seen in the beaker as the composition was being made. Continual foaming also was displayed when the composition was applied to an inanimate surface and let to sit for a few minutes. Thus, a terpene was unable to stabilize the at least partially fluorinated compounds.

Example 10

In this example, personal care compositions containing an oil phase having at least one terpene alcohol and an at least partially fluorinated compound were prepared. The composition components are listed in Table 8.

TABLE 8

Example Composition J

| Trade name | INCI name | Composition Wt. % |
|---|---|---|
| Water | Water | 28% |
| Structure XL | Hydroxypropyl Starch Phosphate | 3.0% |
| Xanthan Gum | Xanthan Gum | 0.35% |
| Ultragel 300 | Polyquaternium-37 | 0.1% |
| Glycerin | Glycerin | 1.0% |
| Miracare SLB 205 | Water, Sodium Trideceth Sulfate, Sodium Lauroamphoacetate, Sodium Chloride, Methylisothiazolinone | 35% |
| 3M Cosmetic Fluid CF-76 | Ethyl Perfluorobutyl Ether, Ethyl Perfluoroisobutyl Ether | 19.5% |
| Lavender Oil | Lavender Oil | 10.0% |
| Butylated Hydroxytoluene | BHT | 0.05% |
| Sodium Benzoate | Sodium Benzoate | 0.5% |
| Sodium Chloride | Sodium Chloride | 2.5% |
| Citric Acid | Citric Acid | q.s. pH 4.7 |

To prepare Example Composition J, water is added to a vessel. The polyquaternium-37 was then added and mixed with the water until uniform. Hydroxypropyl starch phosphate was then added and mixed until uniform. The xanthan gum was then added, and the resulting mixture was mixed until uniform. The structured surfactant blend, Miracare SLB 205, was then added and the resulting mixture was mixed until uniform to prepare a surfactant phase. In a separate vessel, lavender oil was added to butylated hydroxytoluene and mixed until the butylated hydroxytoluene melted (heat to 50° C. if necessary) to prepare an oil phase. The main components of lavender oil are linalool, a terpene alcohol and linalyl acetate. The oil phase was then added to the surfactant phase. Subsequently, the cosmetic fluid, salt and sodium benzoate were added, and the resulting mixture was mixed until uniform. The pH of Example Composition J was adjusted to about 4.7 using citric acid, as needed.

Example Composition J described in Table 8 became very thick and there were larger lumps of gel which effectively stabilized the fluorocarbon both during processing and upon resting in the atmosphere. The gelled composition provided a significant amount of spontaneous foam on the hands when used. However, all of the fluorocarbon/essential oil was not trapped within the surfactant matrix and the untrapped portion accumulated around the gelled portion of the composition. No spontaneous foaming was seen during the entire production process. As the linalool and linalyl acetate are both linear structures and not rings like the rest of the components, they are less polar by nature than the ring structures which may have some impact on the mechanism of stabilization. Thus, while the structure of the terpene alcohol may be of any shape, terpene alcohols having a ring structure may be preferred.

Example 11

In this example, personal care compositions containing an oil phase having at least one terpene alcohol and an at least partially fluorinated compound were prepared. The composition components are listed in Table 9.

TABLE 9

Example Composition K

| Trade name | INCI name | Composition Wt. % |
|---|---|---|
| Water | Water | 28% |
| Structure XL | Hydroxypropyl Starch Phosphate | 3.0% |
| Xanthan Gum | Xanthan Gum | 0.35% |
| Ultragel 300 | Polyquaternium-37 | 0.1% |
| Glycerin | Glycerin | 1.0% |
| Miracare SLB 205 | Water, Sodium Trideceth Sulfate, Sodium Lauroamphoacetate, Sodium Chloride, Methylisothiazolinone | 35% |
| 3M Cosmetic Fluid CF-76 | Ethyl Perfluorobutyl Ether, Ethyl Perfluoroisobutyl Ether | 19.5% |
| Tea Tree Oil | Tea Tree Oil | 10.0% |
| Butylated Hydroxytoluene | BHT | 0.05% |
| Sodium Benzoate | Sodium Benzoate | 0.5% |
| Sodium Chloride | Sodium Chloride | 2.5% |
| Citric Acid | Citric Acid | q.s. pH 4.7 |

To prepare Example Composition K, water is added to a vessel. The polyquaternium-37 was then added and mixed with the water until uniform. Hydroxypropyl starch phosphate was then added and mixed until uniform. The xanthan gum was then added, and the resulting mixture was mixed until uniform. The structured surfactant blend, Miracare SLB 205, was then added and the resulting mixture was mixed until uniform to prepare a surfactant phase. In a separate vessel, tea tree oil was added to butylated hydroxytoluene and mixed until the butylated hydroxytoluene melted (heat to 50° C. if necessary) to prepare an oil phase. The main components of tea tree oil are Terpinen-4-ol, a terpene alcohol, and γ-terpinene. The oil phase was then added to the surfactant phase. Subsequently, the cosmetic fluid, salt and sodium benzoate were added, and the resulting mixture was mixed until uniform. The pH of Example Composition K was adjusted to about 3.5-4.7 using citric acid.

Example Composition K described in Table 9 appeared to be unstable until the pH was brought down between 3.5-4.7. As the pH was being adjusted, the composition obtained a translucent grey appearance and stopped spontaneously foaming in the beaker. The composition displayed no spontaneous foaming behavior in the beaker or when applied onto an inanimate surface. Some foam was generated on the hands when applied and rubbed, but not as much as with the other stable compositions tested. Not to be bound by any theory, but some of the compounds in the tea tree oils may have been protonated to the alcohol form as the pH was adjusted, allowing the composition to display stable behavior as the pH was adjusted lower.

Example 12

In this example, personal care compositions containing an oil phase having at least one terpene alcohol and an at least partially fluorinated compound were prepared. The composition components are listed in Table 10.

TABLE 10

Example Composition L

| Trade name | INCI name | Composition Wt. % |
|---|---|---|
| Water | Water | 28% |
| Structure XL | Hydroxypropyl Starch Phosphate | 3.0% |
| Xanthan Gum | Xanthan Gum | 0.35% |
| Ultragel 300 | Polyquaternium-37 | 0.1% |
| Glycerin | Glycerin | 1.0% |
| Miracare SLB 205 | Water, Sodium Tridecath Sulfate, Sodium Lauroamphoacetate, Sodium Chloride, Methylisothiazolinone | 35% |
| 3M Cosmetic Fluid CF-76 | Ethyl Perfluorobutyl Ether, Ethyl Perfluoroisobutyl Ether | 19.5% |
| Eucalyptus Oil | Eucalyptus Oil | 10.0% |
| Butylated Hydroxytoluene | BHT | 0.05% |
| Sodium Benzoate | Sodium Benzoate | 0.5% |
| Sodium Chloride | Sodium Chloride | 2.5% |
| Citric Acid | Citric Acid | q.s. pH 4.7 |

To prepare an Example Composition L, water is added to a vessel. The polyquaternium-37 was then added and mixed with the water until uniform. Hydroxypropyl starch phosphate was then added and mixed until uniform. The xanthan gum was then added, and the resulting mixture was mixed until uniform. The structured surfactant blend, Miracare SLB 205, was then added and the resulting mixture was mixed until uniform to prepare a surfactant phase. In a separate vessel, eucalyptus oil was added to butylated hydroxytoluene and mixed until the butylated hydroxytoluene melted (heat to 50° C. if necessary) to prepare an oil phase. The main constituent of eucalyptus oil is 1,8-cineole. The oil phase was then added to the surfactant phase. Subsequently, the Cosmetic Fluid, salt and sodium benzoate were added, and the resulting mixture was mixed until uniform. The pH of Example Composition L was adjusted to about 3.5-4.7 using citric acid.

Example Composition L described in Table 10 went together well, but again the stabilized behavior was more prevalent as the pH was adjusted to pH 4.7. The Composition went from a creamy white coloration to an orange tinted translucent appearance as the pH was adjusted. The composition displayed no signs of instability following the pH adjustment either in the beaker or when placed on a surface. Not to be held to any one theory, but it is thought that this is indicative of the terpenoid, 1,8-cineole, being protonated into alcohol form and suspending the at least partially fluorinated compound. Spontaneous foam was generated when placed on the hands.

Example 13

Comparative

In this example, a composition containing an oil phase having isopropyl palmitate and an at least partially fluorinated compound were prepared. The composition components are listed in Table 11.

TABLE 11

Comparative Composition M

| Trade name | INCI name | Composition Wt. % |
|---|---|---|
| Water | Water | 28% |
| Structure XL | Hydroxypropyl Starch Phosphate | 3.0% |
| Xanthan Gum | Xanthan Gum | 0.35% |
| Ultragel 300 | Polyquaternium-37 | 0.1% |
| Glycerin | Glycerin | 1.0% |
| Miracare SLB 205 | Water, Sodium Tridecath Sulfate, Sodium Lauroamphoacetate, Sodium Chloride, Methylisothiazolinone | 35% |
| 3M Cosmetic Fluid CF-76 | Ethyl Perfluorobutyl Ether, Ethyl Perfluoroisobutyl Ether | 19.5% |
| isopropyl palmitate | isopropyl palmitate | 10.0% |
| Butylated Hydroxytoluene | Butylated Hydroxytoluene | 0.05% |
| Sodium Benzoate | Sodium Benzoate | 0.5% |
| Sodium Chloride | Sodium Chloride | 2.5% |
| Citric Acid | Citric Acid | q.s. ph 4.7 |

To prepare Comparative Composition M, water is added to a vessel. The polyquaternium-37 was then added and mixed with the water until uniform. Hydroxypropyl starch phosphate was then added and mixed until uniform. The xanthan gum was then added, and the resulting mixture was mixed until uniform. The structured surfactant blend, Miracare SLB 205, was then added and the resulting mixture was mixed until uniform to prepare a surfactant phase. In a separate vessel, isopropyl palmitate was added to butylated hydroxytoluene and mixed until the butylated hydroxytoluene melted (heat to 50° C. if necessary) to prepare an oil phase. The oil phase was then added to the surfactant phase. Subsequently, the Cosmetic Fluid, salt and sodium benzoate were added, and the resulting mixture was mixed until uniform. The pH of Comparative Composition M was adjusted to about 3.5-4.7 using citric acid.

Comparative Composition M illustrates that the results seen are not the result of just adding a miscible oil to the at least partially fluorinated compound as the example was made with isopropyl palmitate, an ester that is known to be miscible with the fluorocarbon fluid. The composition spontaneously foamed during production. After the composition was made, the product continued foaming in the beaker as well as when product was applied to an inanimate surface. No stability was seen in the composition due to the addition of isopropyl palmitate.

Example 14

In this example, personal care compositions containing an oil phase having at least one terpene alcohol and an at least partially fluorinated compound in the presence of an emulsifier were prepared. The composition components are listed in Table 12.

TABLE 12

Example Composition N

| Trade name | INCI name | Composition Wt. % |
|---|---|---|
| Water | Water | 70.05% |
| Viscarin SD 389 | Carageenan | 0.4% |
| TIC Prehydrated Xanthan Gum | Xanthan Gum | 0.05% |

TABLE 12-continued

Example Composition N

| Trade name | INCI name | Composition Wt. % |
|---|---|---|
| 3M CF 76 Cosmetic Fluid | Ethyl Perfluorobutyl Ether Ethyl Perfluoroisobutyl Ether | 19.5% |
| Menthol | Menthol | 5% |
| Velvetex BA 35 | Cocamidopropyl Betaine | 5% |

To prepare an Example Composition N, water is added to a vessel. The carregeenan and xantham gum were then added and mixed with the water until uniform at 40° C. In a separate vessel, the cosmetic fluid was added to menthol and the resulting mixture was mixed until uniform at 40° C. The two components were slowly mixed together. While slowly mixing, an emulsifier, cocamidopropyl betaine, was added to the mixture and mixed until uniform while at room temperature.

Example Composition N was translucent until the addition of the emuslifier. Upon addition, the formulation formed a lotion appearance. The formulation retained this appearance over several hours with no visible separation of volatile agent. After approximately 60 hours of being left on the benchtop, Example Composition N still had a lotion appearance with some separation of the volatile agent to the bottom of the beaker. When Example Composition N from the top of the beaker is placed on hands and rubbed, spontaneous foaming is observed, illustrating that the at least partially fluorinated compound is stabilized by the menthol within an emulsifier.

Having described the disclosure in detail, it will be apparent that modifications and variations are possible without departing from the scope of the disclosure defined in the appended claims.

The invention claimed is:

1. A foaming personal care composition comprising:
   a carrier;
   an oil phase containing at least one terpene alcohol component;
   an at least partially fluorinated compound selected from ethyl perfluoroisobutyl ether, ethyl perfluorobutyl ether, methyl perfluoroisobutyl ether, methyl perfluorobutyl ether, perfluorodecalin, perfluorohexane, perfluoroheptane, perfluorohexylethyl dimethylbutyl ether, perfluorodimethylcyclohexane, perfluoromethylcyclohexane, perfluoromethyl-cyclopentane, perfluorocyclohexyl methanol, and combinations thereof; wherein the at least partially fluorinated compound is stable within the formulation; and
   a stabilizer;
   wherein the composition has a pH ranging from about 3.5-4.7 and the at least partially fluorinated compound and the terpene alcohol component have a weight ratio of about 4:1.

2. The foaming personal care composition of claim 1 wherein the terpene alcohol component is selected from linalool, geraniol, citronellol, nerol, α-terpene alcohol, borneol, terpinen-4-ol, limonen-4-ol, carveol, lavandulol, menthol, 8-p-cymenol, pinanol, dihydromyrcenol, myrcenol, dihydrolinalool, isomenthol, neomenthol, isopulegol, trans-p-menthane-3,8-diol, isoborneol, globulol, cedrol, menth-1-en-9-ol, sobrerol, umbellulol, nerolidol, pinanediol, farnesol, frenchyl alcohol, eugenol, phytol, isophytol, phytantriol, and combinations thereof.

3. The foaming personal care composition of claim 1 wherein the terpene alcohol component comprises menthol.

4. The foaming personal care composition of claim 1 comprising between about 0.1% and 20% by weight of the composition of the terpene alcohol component.

5. The foaming personal care composition of claim 1 wherein the terpene alcohol component has a ring structure.

6. The foaming personal care composition of claim 1 wherein the terpene alcohol component comprises a terpenoid converted to the terpene alcohol component.

7. The foaming personal care composition of claim 6 wherein the terpenoid is converted to the terpene alcohol by the addition of an acid to the foaming personal care composition.

8. The foaming personal care composition of claim 1 further comprising between about 0.5% and 40% by weight of the composition of the at least partially fluorinated compound.

9. The foaming personal care composition of claim 1 wherein the stabilizer is an emulsifier selected from anionics, nonionics, cationics, amphoterics, zwitteronics, and combinations thereof.

10. The foaming personal care composition of claim 9 wherein the emulsifier is selected from polysaccharide ethers, polyglycosides, fatty acid derivatives, fatty alcohols, amine oxides, water-soluble cellulose derivatives, alkyl sulfonates, ethoxylated alkyl phenols, alkanaolamides, betaines, carboxylated alcohols, carboxylic acids, ethoxylated alcohols, and derivatives and combinations thereof.

11. The foaming personal care composition of claim 9 wherein the emulsifier comprises between 0.1% and 20% by weight of the composition.

12. The foaming personal care composition of claim 1 wherein the stabilizer is a structured surfactant system.

13. The foaming personal care composition of claim 12 wherein the structured surfactant system comprises at least one anionic surfactant, and at least one electrolyte.

14. The foaming personal care composition of claim 13 wherein the structured surfactant further comprises at least one alkanolamide.

15. The foaming personal care composition of claim 1 wherein the carrier comprises water.

16. A foaming lotion comprising:
   a carrier;
   an oil phase containing at least one terpene alcohol component;
   an at least partially fluorinated compound selected from ethyl perfluoroisobutyl ether, ethyl perfluorobutyl ether, methyl perfluoroisobutyl ether, methyl perfluorobutyl ether, perfluorodecalin, perfluorohexane, perfluoroheptane, perfluorohexylethyl dimethylbutyl ether, perfluorodimethylcyclohexane, perfluoromethylcyclohexane, perfluoromethyl-cyclopentane, perfluorocyclohexyl methanol, and combinations thereof; wherein the at least partially fluorinated compound is stable within the formulation; and
   an emulsifier;
   wherein the composition has a pH ranging from about 3.5-4.7 and the at least partially fluorinated compound and the terpene alcohol component have a weight ratio of about 4:1.

17. The lotion of claim 16 wherein the terpene alcohol component is selected from linalool, geraniol, citronellol, nerol, α-terpene alcohol, borneol, terpinen-4-ol, limonen-4-ol, carveol, lavandulol, menthol, 8-p-cymenol, pinanol, dihydromyrcenol, myrcenol, dihydrolinalool, isomenthol, neomenthol, isopulegol, trans-p-menthane-3,8-diol, isoborneol, globulol, cedrol, menth-1-en-9-ol, sobrerol, umbellulol, nerolidol, pinanediol, farnesol, frenchyl alcohol, eugenol, phytol, isophytol, phytantriol, and combinations thereof.

18. The lotion of claim 16 comprising between about 0.1% and 20% by weight of the composition of the terpene alcohol component.

19. The lotion of claim 16 wherein the terpene alcohol component has a ring structure.

20. The lotion of claim 16 wherein the terpene alcohol component comprises a terpenoid converted to the terpene alcohol component.

21. The lotion of claim 16 further comprising between about 0.5% and 40% by weight of the composition of the at least partially fluorinated compound.

22. The lotion of claim 16 wherein the emulsifier is selected from betaines, polysaccharide ethers, polyglycosides, fatty acid derivatives, fatty alcohols, amine oxides, water-soluble cellulose derivatives, alkyl sulfonates, ethoxylated alkyl phenols, alkanaolamides, carboxylated alcohols, carboxylic acids, ethoxylated alcohols, and derivatives and combinations thereof.

23. The lotion of claim 16 wherein the emulsifier comprises between 0.1% and 20% by weight of the composition.

* * * * *